United States Patent
Li et al.

(10) Patent No.: US 11,498,859 B2
(45) Date of Patent: Nov. 15, 2022

(54) COMPOSITION AND METHOD FOR STABILIZING IRON COMPOUNDS IN AN AQUEOUS ENVIRONMENT, AND USE OF COMPOSITION

(71) Applicant: Kemira Oyj, Helsinki (FI)

(72) Inventors: Fengyang Li, Shanghai (CN); Yan Xu, Shanghai (CN)

(73) Assignee: Kermira Oyj, Helsinki (FI)

( * ) Notice: Subject to any disclaimer, the term of this patent is extended or adjusted under 35 U.S.C. 154(b) by 73 days.

(21) Appl. No.: 16/963,272

(22) PCT Filed: Feb. 27, 2018

(86) PCT No.: PCT/CN2018/077461
§ 371 (c)(1),
(2) Date: Jul. 20, 2020

(87) PCT Pub. No.: WO2019/165582
PCT Pub. Date: Sep. 6, 2019

(65) Prior Publication Data
US 2020/0354248 A1    Nov. 12, 2020

(51) Int. Cl.
*C02F 5/14* (2006.01)
*C02F 1/68* (2006.01)
*C23F 11/14* (2006.01)
*C02F 101/20* (2006.01)
*C02F 103/28* (2006.01)
(Continued)

(52) U.S. Cl.
CPC ............. *C02F 5/14* (2013.01); *C02F 1/68* (2013.01); *C23F 11/14* (2013.01); *C02F 2101/203* (2013.01); *C02F 2103/28* (2013.01); *C02F 2303/08* (2013.01); *C07C 211/00* (2013.01);
(Continued)

(58) Field of Classification Search
None
See application file for complete search history.

(56) References Cited

U.S. PATENT DOCUMENTS 4,409,121 A  *  10/1983  Latos .................. C02F 5/145
                                                        106/14.12
4,614,646 A     9/1986  Christiansen
(Continued)

FOREIGN PATENT DOCUMENTS

CN        101700936 A      5/2010
CN        103420514 A      12/2013
(Continued)

OTHER PUBLICATIONS

Translation of CN 107720984A, pp. 1-11. (Year: 2018).*
(Continued)

*Primary Examiner* — Clare M Perrin
(74) *Attorney, Agent, or Firm* — Meunier Carlin & Curfman LLC

(57) ABSTRACT

A composition for stabilizing iron compounds in an aqueous environment, includes a polycarboxylic acid or its salt(s), at least one monomeric or polymeric phosphonate including at least one phosphonic acid group, or its salt(s), at least one corrosion inhibitor including amino groups, and 1-15 weight-% of polycitric acid or a copolymer of citric acid with polyols or glycerol, calculated as an active ingredient from a total weight of constituents in the composition, as dry.

12 Claims, 1 Drawing Sheet

(51) Int. Cl.
- *C07F 9/36* (2006.01)
- *C08F 20/06* (2006.01)
- *C08F 220/06* (2006.01)
- *C07C 211/00* (2006.01)
- *C07F 9/38* (2006.01)

(52) U.S. Cl.
CPC ............... *C07F 9/38* (2013.01); *C08F 20/06* (2013.01); *C08F 220/06* (2013.01)

(56) References Cited

U.S. PATENT DOCUMENTS

| | | | |
|---|---|---|---|
| 4,798,675 A * | 1/1989 | Lipinski | C23F 11/10 210/700 |
| 5,256,303 A | 10/1993 | Zeiher et al. | |
| 5,358,640 A | 10/1994 | Zeiher et al. | |
| 5,683,588 A | 11/1997 | Pomrink et al. | |
| 6,337,047 B1 | 1/2002 | Charkhutian et al. | |
| 6,835,702 B2 | 12/2004 | Herdt et al. | |
| 8,071,067 B2 | 12/2011 | Eskilsson et al. | |
| 2006/0237684 A1 | 10/2006 | Myers et al. | |
| 2011/0114564 A1 | 5/2011 | Amjad et al. | |
| 2014/0360943 A1 | 12/2014 | Aulick | |
| 2015/0004054 A1* | 1/2015 | Richardson | C02F 5/083 422/15 |

FOREIGN PATENT DOCUMENTS

| | | | | |
|---|---|---|---|---|
| CN | 104030461 A | | 9/2014 | |
| CN | 104628157 A | | 5/2015 | |
| CN | 107720984 A | * | 2/2018 | ............ C23F 11/10 |
| CN | 107720984 A | | 2/2018 | |
| RU | 2012541 C1 | | 5/1994 | |
| RU | 2255053 C1 | | 6/2005 | |
| RU | 2334689 C2 | | 9/2008 | |

OTHER PUBLICATIONS

Zarnegar, Zohre et al., "Modified chemical coprecipitation of magnetic magnetite nanoparticles using linear-dendritic copolymers," Green Chemistry Letters and Reviews, published online Aug. 7, 2017, pp. 235-240, vol. 10, Issue 4.

Search Report of corresponding Russian Application No. 2020127916/04(049581), dated Jan. 28, 2021, 2 pages.

Supplementary Search Report of corresponding EP patent application EP 18907545.0, dated Sep. 8, 2021, 3 pages.

Search report dated May 11, 2021 in corresponding application CN 201880093264, 2p.

Allowance Notification dated Aug. 24, 2022, by the EPO in corresponding EP Application No. 18907545.0, 7 pages.

* cited by examiner

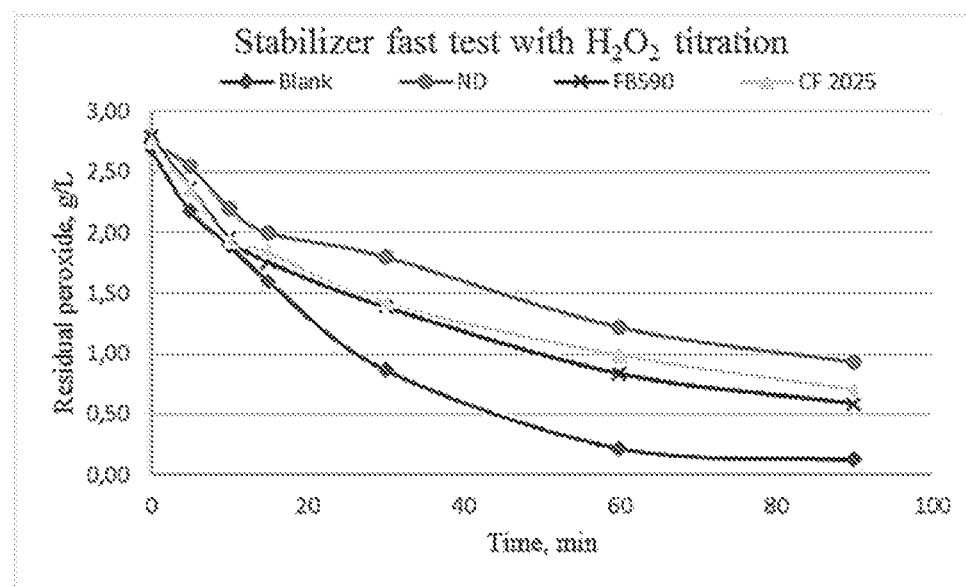

COMPOSITION AND METHOD FOR STABILIZING IRON COMPOUNDS IN AN AQUEOUS ENVIRONMENT, AND USE OF COMPOSITION

PRIORITY

This application is a U.S. national application of the international application number PCT/CN2018/077461 filed on Feb. 27, 2018 the contents of all of which are incorporated herein by reference.

TECHNICAL FIELD

The invention relates to a composition and a method for stabilizing iron compounds in an aqueous environment. The invention also relates to the use of said composition as iron dispersant or iron chelating agent.

BACKGROUND ART

Iron is always existing in water and it could form deposit in the equipment and pipeline. The deposited iron may result in corrosion of metal pipes or equipment. Therefore, deposition of iron is a problem especially in water treatment industry. Dispersant for iron, which may disperse iron compound, is typically employed in water treatment industry. The most suitable dispersants can be chosen on the grounds of the requirements. Different dispersants have effect on different chemicals, such as iron, manganese, calcium carbonate or calcium sulfate. For water treatment industry, diethylenetriamine penta(methylene phosphonic acid) (DTPMPA) is one of typically used dispersants. However, a high phosphorus content of DTPMPA may have negative impact on environment.

In pulp and paper manufacturing, iron coming from wood and from the process equipment is a problem in pulp bleaching. Hydrogen peroxide is widely used as a bleaching agent for different mechanical and chemi-mechanical pulps. Using hydrogen peroxide it is possible to improve pulp brightness. Iron and manganese are the main catalysts for the decomposition of hydrogen peroxide. The decomposition of hydrogen peroxide results in deterioration of fibers, lower whiteness and brightness, and increased consumption of hydrogen peroxide. To reach the required ISO brightness, higher peroxide consumption is needed when iron exists in bleaching process. Therefore, specific chelating steps are included into the chemical pulp process, usually prior to bleaching stages, for eliminating effects of iron and manganese. To detect the efficiency of the deactivation of the metals, usually the pulp properties such as brightness result and viscosity are measured. Also, the residual hydrogen peroxide after bleaching is informative. Phosphonates are typically used as efficient chelating agents in those steps. However, the effectiveness of phosphonates might be insufficient, and the hydrogen peroxide consumption cannot be reduced remarkably. In the case of mechanical pulp, iron and manganese may be deactivated by complexing them with monomeric or polymeric complexing agents. This is done to prevent these metal ions from catalyzing the decomposition of hydrogen peroxide. Commonly, DTPMPA is also used as iron chelating agent in pulp and paper industry.

However, there is a constant need for cost effective and environmentally benign compositions for stabilizing iron compounds in water treatment and/or in pulp bleaching processes.

SUMMARY OF INVENTION

An object of this invention is to minimise or even totally eliminate the disadvantages existing in the prior art.

An object of the invention is to provide a stable composition for stabilizing iron compounds in an aqueous environment. Especially, an object of the invention is to provide a composition suitable for use as iron dispersant in water treatment for controlling, preventing and/or reducing the formation of iron deposit.

Further, it is an object of the present invention to provide a composition suitable for use as iron chelating agent in pulp bleaching for stabilizing hydrogen peroxide and so providing a cost-effective method for preventing hydrogen peroxide degradation due to iron catalysis in bleaching processes.

In order to achieve among others the objects presented above, the invention is characterized by what is presented in the characterizing parts of the enclosed independent claims.

Some preferred embodiments of the invention will be described in the other dependent claims.

The embodiments and advantages mentioned in this text relate, where applicable, both to the composition, the method as well as to the uses according to the invention, even though it is not always specifically mentioned.

A typical composition according to the invention for stabilizing iron compounds in an aqueous environment comprises
- a polycarboxylic acid or its salt(s),
- at least one monomeric or polymeric phosphonate comprising at least one phosphonic acid group, or its salt(s),
- at least one corrosion inhibitor comprising amino groups, and
- 1-15 weight-% of polycitric acid or a copolymer of citric acid with polyols or glycerol, calculated as active ingredient from the total weight of the constituents in the composition, as dry.

BRIEF DESCRIPTION OF THE DRAWINGS

FIG. 1 shows the results obtained in Example 1 of the present application.

DETAILED DESCRIPTION OF THE INVENTION

According to the present invention, the composition for stabilizing iron compounds in an aqueous environment is typically used for controlling and preventing the formation of iron deposit and/or dissolving iron deposits in an aqueous system, especially in water treatment processes. Further, the composition according to the present invention is also used for stabilizing hydrogen peroxide in pulp bleaching process, since adding the composition according to the present invention in oxidation could efficiently prevent hydrogen peroxide degradation due to iron catalysis. Therefore, iron chelation by using the composition according to the present invention in pulp bleaching may decrease $H_2O_2$ consumption.

Typical method according to the present invention for stabilizing iron compound in an aqueous system comprises adding the composition according to the present invention to an aqueous system.

Now, it has been surprisingly found that polycitric acid or a copolymer of citric acid with polyols or glycerol in combination with monomeric or polymeric phosphonate, such as PAPEMP, provides synergetic effect and so the composition according to the present invention is able to provide several advantages simultaneously compared to the commonly used DTPMPA, such as high temperature tolerance and high efficiency even at low dosage amounts of the composition. Thus, the composition according to the present invention provides cost effective iron dispersant composition with high efficiency for use as water treatment systems or iron chelating agent composition for use in pulp bleaching processes. The composition according to the present invention has also remarkably less phosphorus content than the commonly used DTPMPA, and so the present invention also reduces negative impact on environment.

Iron dispersant composition refers in this description to a composition to prevent or reducing fouling of iron oxides/hydroxides in process equipment in water treatment processes. The mechanism of the iron dispersant may be based on dispersing of the iron deposits, or preventing iron compounds to settle, precipitate or agglomerate. Iron dispersant according to the present invention is not only effective for iron, but also have efficiency in calcium carbonate deposit control. Therefore, especially in water treatment industry, it provides multi-function on deposit control.

In paper and pulp industry, peroxide consumption speed in bleaching may be decreased greatly by using the composition according to the present invention as iron chelating agent. When adding composition according to the present invention in oxidation, it could efficiently stabilize hydrogen peroxide and prevent hydrogen peroxide degradation due to iron catalyzing.

The composition according to the invention comprises at least one monomeric or polymeric phosphonate comprising at least one phosphonic acid group. The phosphonate may also comprise any suitable salt(s) thereof. The phosphonate may be selected from hydroxyethylene diphosphonic acid (HEDP), amino tris(methylenephosphonic acid) (ATMP), 2-phosphonobutane-1,2,4,-tricarboxylic acid (PBTC), diethylenetriamine penta(methylene phosphonic acid) (DTPMPA), hexamethylenediamine tetramethylene phosphonic acid (BHMTPMPA), polyamino polyether methylene phosphonic acid (PAPEMP) or any combination of them. According to one preferable embodiment, the phosphonate is polyamino polyether methylene phosphonic acid (PAPEMP) due to its good chelation characteristics. The total amount of the monomeric or polymeric phosphonate(s), such as PAPEMP, may be in the range of 10-90 weight-%, preferably 60-90 weight-%, and more preferably 70-80 weight-%, calculated from the total weight of the constituents in the composition, as dry.

The composition of the invention further comprises a polycarboxylic acid or its salt(s) for providing high temperature tolerant performance and good dispersant performance. According to one embodiment of the invention, the polycarboxylic acid is selected from poly(meth)acrylic acid, or a copolymer of (meth)acrylic acid and maleic acid, itaconic acid or lactic acid. According to one preferred embodiment of the invention, the polycarboxylic acid is poly(meth)acrylic acid. The polycarboxylic acid may have a weight average molecular weight MW less than 5000 g/mol, preferably in a range of 1000-5000 g/mol. The molecular weights are determined by using gel permeation chromatography (GPC). According to one embodiment of the invention, the amount of the polycarboxylic acid is in the range of 5-80 weight-%, preferably 20-50 weight-% and more preferably 20-30 weight-%, calculated from the total weight of the constituents in the composition, as dry.

Further, the composition according to the present invention comprises at least one corrosion inhibitor comprising amino groups. The amount of the corrosion inhibitor may be in the range of 2-10 weight-%, calculated from the total weight of the active constituents in the composition, as dry. According to an embodiment of the invention the corrosion, the inhibitor is selected from diethyl hydroxylamine (DEHA), octadecylamine, hexadecylamine, cyclohexylamine, methoxypropylamine, other fatty alcohol amines, or any combination of them. According to one preferred embodiment, the corrosion inhibitor is diethyl hydroxylamine (DEHA) due to its excellent iron corrosion inhibition performance and efficiency even at small dosage amount.

The composition according to the present invention comprises also polycitric acid or a copolymer of citric acid with polyols or glycerol. According to a preferred embodiment of the invention, the composition comprises polycitric acid, which is obtained by polymerization using citric acid as raw material. Therefore, the composition according to the invention includes two kinds of carboxylic acid, i.e. polycitric acid and polycarboxylic acid or its salt(s) as defined above. The amount of polycitric acid or a copolymer of citric acid with polyols or glycerol may be in the range of 1-15 weight-%, calculated as active ingredient from the total weight of the constituents in the composition, as dry. According to one preferred embodiment of the invention, the amount of polycitric acid or a copolymer of citric acid with polyols or glycerol is less than 15 weight-%, calculated as active ingredient from the total weight of the constituents in the composition, as dry. In some preferred embodiments, the amount of polycitric acid or a copolymer of citric acid with polyols or glycerol is in the range of 5-10 weight-%, calculated as active ingredient from the total weight of the constituents in the composition, as dry, when optimising the effect and total costs of the composition. Preferably, the composition according to the present invention comprises polycitric acid in an amount of 1-15 weight-% or 5-10 weight-%, calculated from the total weight of the constituents in the composition, as dry, and this amount is not included to the amount of the polycarboxylic acid or its salt(s) defined separately in the present application.

According to an embodiment of the invention, a copolymer of citric acid with polyols or glycerol may be poly(citric acid-glycol) ester, poly(citric acid-ethylene glycol) ester, poly(citric acid-propylene glycol) ester, poly(citric acid-glycerol) ester or poly(citric acid-triethanolamine) ester prepared by subjecting a raw material selected from the group consisting of a mixture of citric acid and glycol, a mixture of citric acid and ethylene glycol, a mixture of citric acid and propylene glycol, a mixture of citric acid and glycerol and a mixture of citric acid and triethanolamine to condensation polymerization. The synthetization of polycitric acid or a copolymer of citric acid with polyols or glycerol applicable to be used in the composition of the present invention is described e.g. in the patent publication CN104030461.

As also disclosed in CN104030461, polycitric acid may be synthesized by condensation polymerization by using citric acid as raw material. Tetrahydrofuran is used as a solvent, wherein the solvent and citric acid are added in a reactor and the solution is obtained by mixing. Concentrated sulfuric acid is used as a catalyst and added to the solution of the solvent and citric acid and heated to the reflux state to perform condensation polymerization for 4-24 h to obtain the reaction solution. The reaction solution is further neutralized, transferred to extraction and rotary evaporation steps. Organic solvent is removed by rotary evaporation and the obtained polycitric acid is dark brown slime having substantially 100% content of polycitric acid.

According to one preferred embodiment, the composition comprises 5-80 weight-% of poly(meth)acrylic acid, 10-90 weight-% of PAPEMP, 2-10 weight-% of DEHA, and 1-15 weight-% of polycitrc acid, calculated from the total weight of the constituents in the composition, as dry. More preferably, the composition comprises 60-90 weight-% or 70-80 weight-% of PAPEMP in combination with poly(meth)acrylic acid, DEHA and polycitric acid. In one preferred embodiment, the composition comprises 60-90 weight-% or 70-80 weight-% of PAPEMP, 20-50 weight-% or 20-30 weight-% of poly(meth)acrylic acid, 2-10 weight-% of DEHA and 1-15 weight-% of polycitric acid, calculated from the total weight of the constituents in the composition, as dry.

The composition according to the invention tolerates high temperatures, i.e. it is effective also in high temperatures, and so it may be added to the industrial aqueous systems having temperature of the aqueous phase higher than 100° C. The temperature of the aqueous phase in the aqueous system, where the composition is dosed, may be over 100° C., or over 120° C., or even over 200° C.

According to the invention, the composition is added to an aqueous system. The composition according to the invention may be used in desired dose, depending on the nature of the iron compounds to be stabilized and/or other conditions in the aqueous system where it is used. For example, according to one embodiment of the invention the composition may be added in an amount of 5-100 ppm, preferably 5-70 ppm, and more preferably 5-50 ppm to an aqueous system.

The composition according to the present invention may be used at any process stage of suitable application, where there is a risk for iron deposit formation. According to one embodiment of the invention, the composition according to the present invention may be used for reducing or eliminating the formation of iron deposit in the water treatment systems.

The composition according to the present invention may be used at bleaching process for stabilizing hydrogen peroxide. It may be added to the pulp prior to bleaching stages.

EXPERIMENTAL

Example 1: Iron Dispersion Performance Evaluation in Water

Solution A cationic $CaCl_2$ liquid, $Ca^{2+}$ concentration is 300 ppm;
Solution B: Selected scale inhibitor is diluted according to a certain concentration;
Solution C: 5 g $(FeSO_4.7H_2O)/l$, fresh;
Solution D: 500 ppm $Na_2B_4O_2$ liquid.
Blank test: 50 ml solution A+12 ml deionized water+1 ml solution C+37 ml solution D.
Scale inhibition test sample: 50 ml solution A+12 ml deionized water+selected solution B+1 ml solution C+37 ml solution D, pH about 8.7.

After all the chemicals of each sample are added into the bottle, the bottles are stirred for 15 min. Then, the bottles are put into the water bath and heated for 20 h. The bottles are taken out from the water bath and stood for 1 hour. The solution from each bottle is filtered and $Ca^{2+}$ concentration in the filtrates are determined using inductively coupled plasma (ICP) instrument. Fe content is analyzed from the supernatant by using ICP.

Iron dispersant capability calculation (%):

$$\eta(\text{iron dispersant}) = \frac{X2 - X1}{10 - X1},$$

wherein
X1 is Iron concentration (mg/l) in blank sample before treatment,
X2 is Iron concentration (mg/l) after treatment,
10 is Iron preliminary concentration (mg/l).

The performance evaluation is carried out by using the following scale inhibitors: the composition according to the present invention (ND), commercial iron dispersant products Kemguard 5876 (Acrylic acid terpolymer, sodium salt) and Kemguard 5042 (Polycarboxylate, sodium salt) from Kemira, PBTC, BHMPTMPA, HPMA, POCA and DTPMPA as solution B. The ND composition according to the present invention comprises 5-80 weight-% of poly(meth)acrylic acid, 10-90 weight-% of PAPEMP, 2-10 weight-% of DEHA and 1-15 weight-% of polycitric acid, calculated from the total weight of the constituents in the composition, as dry.

The performance of the dispersant compositions is tested at two different temperatures 50° C. and 90° C. Also, two different concentrations, namely 10 ppm and 20 ppm, are tested. The results are shown in Table 1 and Table 2.

TABLE 1

The results of Iron dispersion performance at 50° C.

| | Iron dispersant capability calculation (%) | |
|---|---|---|
| Dispersant | 10 ppm | 20 ppm |
| Blank test | 1.12 | 1.12 |
| Kemguard 5876 | 2.10 | 3.16 |
| Kemguard 5042 | 3.40 | 3.45 |
| PBTC | 4.86 | 3.60 |
| BHMPTMPA | 2.82 | 2.96 |
| HPMA | 2.52 | 3.42 |
| POCA | 3.25 | 3.21 |
| DTPMPA | 7.88 | 13.21 |
| ND | 13.59 | 69.40 |

TABLE 2

The results of Iron dispersion performance at 90° C.

| | Iron dispersant capability calculation (%) | |
|---|---|---|
| Dispersant | 10 ppm | 20 ppm |
| Blank test | 0.28 | 0.28 |
| Kemguard 5876 | 0.66 | 0.45 |
| Kemguard 5042 | 0.61 | 0.63 |
| PBTC | 0.79 | 4.04 |
| BHMPTMPA | 1.04 | 1.89 |
| HPMA | 1.05 | 1.57 |
| POCA | 0.77 | 0.95 |
| DTPMPA | 23.25 | 31.51 |
| ND | 78.86 | 82.76 |

From the experiment results, it can be seen that the ND material efficiency is much better than other compositions.

Example 2: The Effect of Stabilizer on Alkaline $H_2O_2$ Bleaching

The peroxide stability test is used to determine the peroxide content in a water solution containing specific amount of Fe ions and monitor the peroxide decomposition rate. The test is performed in Erlenmeyer flasks. The dilution water is heated to 90° C. before adding 11 ppm Fe ions and the 100 ppm stabilizer composition to be tested. The pH is adjusted with NaOH to pH 10 before adding peroxide (initial peroxide content 3 g/l). The residual peroxide (g/l) in the sample is titrated after 5, 10, 15, 30, 60 and 90 min.

The following stabilizers are used in the tests: the composition according to the present invention (ND), commercial stabilizer products Fennobrite FB590 from Kemira and CF2025 from Kemira, which comprise phosphonates. The ND composition according to the present invention comprises 5-80 weight-% of poly(meth)acrylic acid, 10-90 weight-% of PAPEMP, 2-10 weight-% of DEHA and 1-15 weight-% of polycitric acid, calculated from the total weight of the constituents in the composition, as dry.

The results are shown in FIG. 1. Compared with FB 590 and CF 2025, the ND composition according to the present invention has better performance in $H_2O_2$ stabilizing.

Even if the invention was described with reference to what at present seems to be the most practical and preferred embodiments, it is appreciated that the invention shall not be limited to the embodiments described above, but the invention is intended to cover also different modifications and equivalent technical solutions within the scope of the enclosed claims.

The invention claimed is:

1. A method to stabilize iron compounds in an aqueous system, comprising adding to the aqueous system a composition comprising:
   a polycarboxylic acid or its salt(s) selected from poly(meth)acrylic acid or a copolymer of (meth)acrylic acid and maleic acid, itaconic acid or lactic acid;
   60-90 weight-% of polyamino polyether methylene phosphonic acid (PAPEMP), calculated from a total weight of constituents in the composition as dry;
   a corrosion inhibitor selected from diethyl hydroxylamine (DEHA), octadecylamine, hexadecylamine, cyclohexylamine, methoxypropylamine, fatty alcohol amines, or any combinations thereof; and
   1-15 weight-% of polycitric acid, calculated as an active ingredient from a total weight of constituents in the composition as dry.

2. The method according to claim 1, wherein the composition is added in an amount of 5-100 ppm.

3. The method according to claim 2, wherein the composition is added in an amount of 5-70 ppm.

4. The method according to claim 3, wherein the composition is added in an amount of 5-50 ppm.

5. The method according to claim 1, wherein the aqueous system is a water treatment system or forms a part in a pulp bleaching process.

6. The method according to claim 1, wherein the polycarboxylic acid is a poly(meth)acrylic acid.

7. The method according to claim 1, wherein the polycarboxylic acid has a weight average molecular weight (MW) of 5000 g/mol or less, determined by using gel permeation chromatography (GPC).

8. The method of claim 7, wherein polycarboxylic acid has a weight average molecular weight (MW) in a range of 1000-5000 g/mol.

9. The method according to claim 1, wherein the corrosion inhibitor is diethyl hydroxylamine (DEHA).

10. The method according to claim 1, wherein an amount of the polycarboxylic acid in the composition is in a range of 5-30 weight-%, calculated from a total weight of constituents in the composition, as dry.

11. The method according to claim 1, wherein an amount of polyamino polyether methylene phosphonic acid (PAPEMP) is in a range of 70-80 weight-%, calculated from a total weight of the constituents in the composition, as dry.

12. The method according to claim 1, wherein an amount of the corrosion inhibitor in the composition is in a range of 2-10 weight-%, calculated from a total weight of the constituents in the composition, as dry.

* * * * *

UNITED STATES PATENT AND TRADEMARK OFFICE
CERTIFICATE OF CORRECTION

PATENT NO. : 11,498,859 B2
APPLICATION NO. : 16/963272
DATED : November 15, 2022
INVENTOR(S) : Fengyang Li and Yan Xu It is certified that error appears in the above-identified patent and that said Letters Patent is hereby corrected as shown below:

On the Title Page

Item (73) Should Read:
Assignee: Kemira Oyj, Helsinki (FI)

Signed and Sealed this
Fourth Day of April, 2023

Katherine Kelly Vidal
*Director of the United States Patent and Trademark Office*